(12) United States Patent
Flesch et al.

(10) Patent No.: US 7,066,887 B2
(45) Date of Patent: Jun. 27, 2006

(54) BI-PLANE ULTRASONIC PROBE

(75) Inventors: Aimé Flesch, Andrésy (FR); An Nguyen-Dinh, Valleres (FR)

(73) Assignee: Vermon, Tours Cedex (FR)

( * ) Notice: Subject to any disclaimer, the term of this patent is extended or adjusted under 35 U.S.C. 154(b) by 0 days.

(21) Appl. No.: 10/689,081

(22) Filed: Oct. 21, 2003

(65) Prior Publication Data
US 2005/0085730 A1 Apr. 21, 2005

(51) Int. Cl.
A61B 8/00 (2006.01)
A61B 8/12 (2006.01)

(52) U.S. Cl. ................................. 600/447; 600/463
(58) Field of Classification Search ........ 600/459–471; 310/334, 336
See application file for complete search history.

(56) References Cited

U.S. PATENT DOCUMENTS

| | | | |
|---|---|---|---|
| 3,881,164 A | 4/1975 | Kossoff | |
| 4,640,291 A | 2/1987 | 't Hoen | |
| 4,671,293 A | 6/1987 | Shaulov | |
| 4,870,467 A * | 9/1989 | Boland et al. | 257/603 |
| 5,050,610 A * | 9/1991 | Oaks et al. | 600/437 |
| 5,103,129 A | 4/1992 | Slayton et al. | |
| 5,327,895 A * | 7/1994 | Hashimoto et al. | 600/459 |
| 5,410,205 A * | 4/1995 | Gururaja | 310/328 |
| 5,465,724 A | 11/1995 | Sliwa, Jr. et al. | |
| 5,625,149 A * | 4/1997 | Gururaja et al. | 73/632 |
| 5,680,863 A * | 10/1997 | Hossack et al. | 600/459 |
| 5,681,263 A | 10/1997 | Flesch | |
| 5,771,896 A | 6/1998 | Sliwa, Jr. et al. | |
| 6,014,473 A | 1/2000 | Hossack et al. | |
| 6,045,508 A * | 4/2000 | Hossack et al. | 600/447 |
| 6,238,336 B1 | 5/2001 | Ouchi | |
| 6,261,234 B1 | 7/2001 | Lin | |
| 6,364,835 B1 * | 4/2002 | Hossack et al. | 600/443 |
| 6,537,220 B1 * | 3/2003 | Friemel et al. | 600/447 |
| 6,572,547 B1 | 6/2003 | Miller | |
| 6,641,534 B1 * | 11/2003 | Smith et al. | 600/437 |

FOREIGN PATENT DOCUMENTS

EP 0139574 5/1985

OTHER PUBLICATIONS

Shaulov, A. et al "Biplane Phased Array for Ultrasound Medical Imaging" 1988 IEEE Symposium pp. 635-638.*

* cited by examiner

Primary Examiner—Francis J. Jaworski
(74) Attorney, Agent, or Firm—Stites & Harbison PLLC; Ross F. Hunt, Jr.

(57) ABSTRACT

Ultrasonic probe devices are provided which are particularly suitable for use as invasive imaging probes such as endocavity probes and endoscopic probes. The probe devices include a dual cross-scanning bi-plane array transducer formed by a pair of orthogonal, intersecting transducer arrays. The probe devices are capable of providing, either simultaneously or alternately, crossing scanning through a single symmetrical scanning axis.

17 Claims, 11 Drawing Sheets

BI-PLANE ULTRASONIC PROBE

FIELD OF THE INVENTION

The present invention relates to ultrasonic probes, particularly for, but not limited to, use in medical diagnosis.

BACKGROUND OF THE INVENTION

Diagnosing the internal organs of human body by ultrasound is one of the most common modalities used in modern medicine. The ultrasonic waves are non-ionizing and this results in large tolerances as to when ultrasonic waves can be used, e.g., the examination of a fetus. The ultrasonic imaging probes that are particularly dedicated to medical diagnosis can be conveniently divided into two groups: (i) external devices that are used in contact with the skin; and (ii) invasive devices that are employed in circumstances where external scanning results in a lack of precision in the diagnosis or where a higher frequency image is desirable.

In general, external and invasive devices are quite different in terms of design shape and material composition. Indeed, the requirements for the housing materials used in invasive instruments are much stricter than those applied to external instruments. Furthermore, the electrical security of safety level for patients and users must comply with medical regulations for surgical instruments.

The family of invasive ultrasonic imaging probes includes various shapes and designs adapted to fit the internal morphology of the organ to be imaged. A distinction can be made between (i) endocavity probes which are used for endo-vaginal and endo-rectal diagnostics, (ii) endoscopic probes that are elongated versions of invasive instruments wherein the imaging transducer is mounted at the extremity of the (flexible or rigid) tube of an endoscope, which is, in turn, attached to an endoscope handle on which the control functions for the instruments are typically provided, (iii) catheter based probes wherein the ultrasonic transducer is mounted at the extremity or distal end of the corresponding catheter tube, and (iv) special imaging devices designed for specific applications such as brain imaging (e.g., a "Burr Hole" probe) or surgical monitoring (e.g., "Per-Op" probes). Generally speaking, catheter-based instruments for ultrasonic diagnostics are very similar to endoscopic tubes but have a much smaller tube diameter, while Burr Hole type probes are considered to be a customized version of endocavity probe devices. Surgical monitoring (Per-Op) probes are specialized instruments that are specifically designed to fit each particular surgical application. Accordingly, there is a large variety of such instruments, with a small housing being a common characteristic thereof.

Turning first to endoscope-based devices, endoscopic probes are widely used in trans-esophageal echography TEE and intra-vascular imaging (catheter probes). It is evident that the design and shape of diagnostic probes for invasive applications and, more particularly, for endoscopic applications, are governed by the morphology of the organs to be explored; the probes commonly exhibit a long tubular shape to facilitate insertion of the probe into the organ. Generally, the diameter of the tubular portion does not exceed a dozen millimeters (corresponding to the internal diameter of the esophagus).

The above characteristics and features specific to invasive products make them much more expensive and complicated to design and manufacture than conventional diagnosing devices. This is particularly true when the probe is provided with a steering control for the transducer tip during operation (i.e., bending capability) such as is disclosed, for instance, in commonly assigned U.S. Pat. No. 5,681,263 to Flesch. Transducers that are used to equip TEE probes are of high frequency, generally ranging from 5 to 15 MHz. The probe can be provided with a single phased array transducer, dual perpendicular phased array transducers or with a rotated phased array transducer. More recently, some advanced products are based on implementation of a 2D transducer (matrix array).

Similarly to endoscopic ultrasonic devices, ultrasonic probes for endo-rectal and endo-vaginal applications, as well as Burr Hole probes, are built to fit, i.e., to be physically compatible with, the particular organs to be imaged. Generally, such probes are comprised of an external handle and an elongated rigid tube that extends outwardly from the handle and terminates at a transducer tip. The transducer is mounted at the distal extremity of the elongated part of the probe in a manner so as to facilitate accessing of the region of interest. Conventionally, endo-vaginal probes are provided with a curved linear array transducer mounted at the extremity of the tube so as to allow forward scanning of the organ while endo-rectal probes are typically provided with a linear array transducer mounted along with the longitudinal axis of the probe and can be accompanied with a curved array transducer disposed perpendicularly thereto. The frequency of the transducers used in endocavity probes generally ranging from 5 to 10 MHz and the diameter of the inserted part of the probe is typically between 5 and 20 mm.

As indicated above, ultrasonic probes that are designed for use during surgical operations to directly contact human organs are commonly called Per-Op devices. These probes generally comprise an ultrasonic array transducer mounted in a plastic housing that is designed to be sufficiently small and compact so as to be handled by the finger of a surgeon. Several different transducer configurations can be used based on the organ to be imaged and the method of access to the organ that is to be used. Commonly, Per-Op ultrasonic probes are available with the transducer mounted in a probe having a longitudinal, transverse or end-finger configuration. The frequency of the transducer is selected to be suitably high, in a frequency range of about 10 to 20 MHz.

In spite of the use therein of dual transducers, rotating transducers and 2D array transducers, invasive ultrasonic devices still suffer a number of drawbacks and shortcomings with regard to complexity of design, cost of manufacturing and/or lack of reliability. During the past decade, numerous improvements have been made with respect to the basic design of such devices, including, e.g., the provision of rotating phased array transducers, the implementation of 1.5D array transducers for enhancement of the lateral resolution of the images obtained, and the implementation of static 2D transducers as part thereof. The performance and scanning characteristics of such devices have been significantly extended and a corresponding improvement in the resultant diagnostics has resulted. However, the sophistication added to conventional TEE probes has not only enhanced the performance and operating characteristics of the resultant probe but has also raised considerably the manufacturing costs of the probe while simultaneously decreasing the reliability thereof in operation, thereby dramatically increasing the maintenance costs associated with the probe.

It is also noted that endocavity probes that are commonly provided with basic phased array transducers or dual transducer mountings suffer certain limitations in terms of scanning range and the angle of view available during examination. Further, these probes are often used with a biopsy needle for tissue extraction especially in endo-rectal diagnosis, and the accuracy of the placement of biopsy needle is important for the success of the operation. The biopsy needle movement is normally monitored through use of the scanning image, and precise spatial positioning of the needle is desirable to assure that the implicated tissue is sampled. In existing probe devices, a needle guide, which is mechanically secured or fastened to the probe, is provided to enable guiding the needle when the latter is introduced into the tissue. The progression of the needle can observed on the system display unit that provides imaging of the organ, in a scanning plane containing the needle. It will be appreciated that if a misalignment is observed with respect to the biopsy needle, the sampled tissue can be shifted from the theoretical scanning plane without any information being conveyed to the examiner of the organ, i.e., the user of the imaging system. Indeed, as long as the biopsy needle remains within the lateral resolution of the probe, no steering of the needle can be detected by the system.

Currently, TEE probes are generally available with a rotating phased array transducer mounted thereon. The transducer is capable of a rotational movement around the center axis thereof, which is defined as the axis of symmetry of the transducer. This axis also acts as an acoustic energy propagation pathway. Probe devices that include rotating phased array transducers are commonly called "multi plane TEE probes."

With regard to the endocavity probe devices, a wider variety of probes is available and the design can change with different manufacturers. However, the probes remain quite basic and most improvements involve the use of wide angle array transducers or high density arrays.

The prior art includes two groups of multi-plane ultrasonic probes and both groups include TEE and endo-cavity probes.

The first group of prior art probes is principally comprised of ultrasonic imaging devices including at least two separate transducers which are disposed in the vicinity of each other and which are preferably oriented perpendicularly to each other. These ultrasonic transducers are usually provided in phased-array types that are individually phase shift addressed by the electronics of the associated scanner. In practice, this group of probe devices basically includes endo-cavity instruments and some rare TEE probes. The devices generally incorporate different combinations of transducer mountings. These combinations include, for example, two separate aligned phased arrays disposed perpendicularly each other, a linear array disposed perpendicularly to a curved array, a curved array linearly assembled to a phased array, a phased array geometrically combined with a mechanical sector transducer, and the like. All of the probes belonging to this group are generally considered as standard probe products and are quite widespread throughout the market. However, mechanical sector moving transducer probes are much less common than other the types and the trend is toward electronic scanning devices having a single or dual static transducer array.

The second group of probes is comprised of diagnosing instruments having a dynamic multi plane capability. Such probes are provided with a unique phased array transducer capable of a rotating motion around a vertical axis virtually located at the center of the transducer. The scanning plane of the phased array is, therefore, capable of rotating with a predetermined angle from the initial position thereof. The ability of such arrays to provide rotated scanning planes and to recognize the position of each of the planes, has resulted in an enhanced diagnosis in, for example, cardiology where at least two orthogonal images are often required to achieve the desired diagnosis. This capability is achieved either by providing a single phased array transducer rotatable around its own vertical axis, or by using a matrix (2D) array transducer that is theoretically capable of providing scanning planes of a desired orientation. Such dynamic multi-plane features are chiefly employed in TEE probes and in high-end diagnosing probe devices of the type wherein the significant additional increase in purchase price and in maintenance costs are partially compensated for by the improvement in diagnostic ability and the user-friendly characteristics inherently provided. It is noted that matrix based dynamic multi-plane probes have been recently disclosed as concept or engineering prototypes. A commercial product is not available as yet, so that the focus here will be on rotating phased array based diagnosing probes.

Patents of potential interest here include the following: U.S. Pat. No. 3,881,164 to Kossoff; U.S. Pat. No. 4,640,219 to T'Hoen; U.S. Pat. No. 4,671,293 to Shaulov; U.S. Pat. No. 5,163,129 to Slayton; U.S. Pat. No. 5,681,263 to Flesch, U.S. Pat. No. 5,456,724 to Sliwa; U.S. Pat. No. 5,771,896 to Sliwa; U.S. Pat. No. 6,041,473 to Hossack; U.S. Pat. No. 6,238,336 to Ouchi; U.S. Pat. No. 6,261,234 to Lin; U.S. Pat. No. 6,572,547 to Miller; and EP Patent No. 139,574 to Fornage.

As described above, ultrasonic probes for invasive intervention or diagnostics employ various shapes and configurations with regard to transducer implementation. In European Patent EP No. 139,574 to Fornage et al, there is provided an endocavity ultrasonic probe including at least two imaging transducers employed in a manner such as to provide the user with two tomography scanning images derived from the same region of interest. The ultrasonic transducers are generally of an electronic scanning type but can also be mechanically rotated to form a sector scanning plane. Different transducer implementations are disclosed such as a combination of a linear array and a mechanically rotated transducer, two perpendicularly disposed linear arrays, two curved linear perpendicularly disposed arrays, a linear array and a circular array, and the like. The transducers are disposed on the probe housing in close proximity to produce an intersecting region of the two respective scanning planes.

Similarly, U.S. Pat. No. 6,261,234 to Lin describes a method and apparatus for simultaneously viewing a surgical instrument in two ultrasound imaging planes. The patent also relates to medical endocavity probes wherein a working channel for guiding surgical instruments is provided at the distal tip of the probe. Two separate array transducers are disposed orthogonally in order to provide intersection of the surgical instrument at the intersection of the two scanning planes. The drawbacks of such devices principally concern the crowding or encumbrance of the transducer tip portion produced by mounting several array transducers in close proximity, the complexity of the transducer housing and the complexity or intricacy involved in mounting the assembly onto the probe. Further, the transducers are not located in the same area so that the intersecting zone or region can only be achieved at a certain distance with respect to the emission surfaces of the transducers, thus preventing exploitation of the near field of the image.

In U.S. Pat. No. 6,238,336 to Ouchi, a method is provided which allows the observation of a treatment tool inserted into an ultrasonic imaging instrument. A first curved linear array transducer is provided in the medial area of the transducer tip. This linear array transducer is associated with a sector-shaped mechanically-rotated transducer mounted at the distal portion of the transducer tip. The two transducer images cross perpendicularly so as to enable visualization of the treatment tool being introduced along the azimuth plane of the curved array. The combination of an electronic scanning array and a mechanical sector transducer is very similar to that described in the EP No. 139,574, and the shortcomings and disadvantages described previously are also present.

Other references, such as U.S. Pat. Nos. 5,456,724 and 5,771,896 to Sliwa, Jr. et al., disclose a compact rotationally steerable ultrasound transducer. A circular array transducer is mounted on a circular track and can be rotated by a motor disposed in the vicinity thereof. A position detector is also provided for forwarding transducer position information to the associated imaging system.

Similarly, in U.S. Pat. No. 6,572,547 to Miller et al., there is disclosed a TEE transducer tip including a matrix (2D) array transducer that is capable of rotating or moving the scanning planes on the surface of the transducer.

Both of the Sliwa Jr., et al patents relate to dynamic multi-plane transducer devices, and use a rotating phased array in which implementation of a motorized drive and position encoder are required. The alternate rotation of the transducer during the operation thereof is a source of electrical noise or contact wear. Further, the high degree of integration that the device exhibits results in an increase in cost and a lack of reliability.

With regard to the first Sliwa, Jr. et al. patent (the '724 patent), integration of the 2D array transducer is apparently a more reliable process. However, 2D array transducers provide a scanning image quality that is much lower than that obtained with a 1D phased array, and the complexity involved in addressing all elements of such an array would make the device unattractive for many applications.

In conclusion with respect to these types of prior art transducers, whether incorporated in TEE or endo-cavity probes including intravascular and intracardiac devices, current transducer implementation methods such as aforementioned still impose on manufacturers and users a number of constraints that limit the scanning possibilities of the probes and/or considerably increase the manufacturing cost thereof and, furthermore, reduce the reliability of the resultant probe devices.

One technique that is capable of overcoming all of the aforementioned shortcomings, with an acceptable compromise as to the performance and cost of the resultant device, involves the use of an integrated bi-plane phased array transducer. In this kind of transducer, an ultrasound device is provided wherein a first phased array is provided on a first surface of a piezoelectric member of the transducer, and a second phased array, which is rotated by 90° respect to the first array, is provided on the opposite surface of the same piezoelectric member. Such a transducer has been disclosed in prior art with a number of different variations in the design and construction thereof but the transducer is still difficult to implement in practice and the acoustic performance thereof is limited by the lack of efficient isolation between the first and the second arrays as well as between the elements of the same array.

What may be the first disclosure of ultrasonic transducers having first and second separate arrays disposed in an orthogonal fashion is provided in U.S. Pat. No. 3,881,164 to Kossoff, wherein a main linear transducer array intersects a second transducer array at a middle area thereof, so that a portion of the surface of the second array is lost, i.e., is eliminated. This lost portion corresponds to the width of the first array. However, this early conception cannot be considered to be a true bi-plane construction because the second array of the apparatus is very different from the first array and serves in carrying out Doppler functions or positioning operations.

The first disclosures of the bi-plane transducer concept may have been those contained in U.S. Pat. No. 4,640,291 to T'Hoen and U.S. Pat. No. 4,671,293 to Shaulov, wherein bi-plane composite transducers are described. The piezoelectric member can be provided either without element kerfs, as described in the T'Hoen patent, or with partial grooves formed in the thickness of material, as described in the Shaulov patent. The transducer electrodes are plated on both surfaces of the transducer and correspond, respectively, to first and second transducer arrays. The two arrays are, therefore, provided on the same piezoelectric substrate so that the arrays exhibit very similar characteristics. However, it is noted that no interconnection method is disclosed in these patents and the grooving method described therein limits the cross coupling performance of the transducers.

Another approach to obtaining intersecting scanning planes has been disclosed in U.S. Pat. No. 5,103,129 to Slayton et al. wherein an ultrasonic transducer is provided having an elongated body on which a cross-shaped plate of ceramic is mounted. The ceramic is cross-shaped and the cross arms cross at the center of the ceramic. A number of variations of the crossed configurations are disclosed and these generally include a central area at which the crossing transducer arms intersect. The "hot" or active electrodes of both arrays are all provided on the same face of the piezoelectric substrate so that respective elements of the two arrays cross at the center area of the transducer.

In the Slayton et al patent, the addressing scheme or management approach for the center area is discussed in connection with different embodiments such as a crossed section (meaning that the elements of the two arrays are reduced progressively in elevational width going toward the center of the transducer) or a matrix section (wherein electrode grooves or kerfs are provided on the two arrays without attention to the center area, so that a sub-2D array is thus obtained at this central location). The ground electrode is common to both arrays and is disposed at the front surface of the transducer in contact with an acoustic matching layer.

As a result of constructions described above, the bi-plane transducers as disclosed in the Slayton et al. patent suffer several limitations with respect to their manufacture and operation. In this regard, for the crossed section type, both of the arrays suffer from a substantial diminution of the element surface at the center area of the transducer which results in a dramatic loss of sensitivity at the middle portion of the image (or even the absence of an image at the center of the display). This is unacceptable in diagnostic applications and thus such a transducer construction simply cannot be used in clinical applications. With regard to the matrix section embodiment disclosed in the Slayton et al patent, the transducer can essentially be considered to be a 2D array transducer with complementary prominent transducer arms extending in each cardinal direction. The complexity involved in manufacturing and assembling such a device is greater than that discussed above for standard 2D arrays so that a cost effective implementation of such an array, and the associated addressing electronics, in an invasive medical product is difficult to practically achieve.

In summary, while currently available invasive ultrasound products which still use rotating phased array arrangements or separate phased array assemblies suffer significant disadvantages, a bi-plane approach has not been viable for important applications because of difficulties associated with making bi-plane transducers as well as the lack of a viable technical solution with respect to the problem of integrating such a bi-plane transducer into an invasive probe. Consequently, there exists a need in the art for a bi-plane transducer capable of providing comparable performance to a conventional phased array and for an invasive probe that incorporates such a bi-plane transducer therein in a manner so as to provide high quality medical diagnosis.

SUMMARY OF THE INVENTION

One object of the invention is to provide a compact endocavity ultrasound imaging probe (for endo-vaginal, endo-rectal, trans-esophageal endoscopic, intravascular, intracardiac or like use) which includes an intersecting bi-plane phased array transducer mounted at the distal end of the probe so as to provide a sonographer or other user the benefits of uni-axis intersecting scanning planes.

A further object of the invention is to provide a bi-plane phased array transducer which is capable of supplying intersecting images having the same acoustic characteristics.

Still another object of the invention is to provide a single bi-plane phased array transducer which enables the associated probe to be equipped with working channels for the insertion of biopsy and surgical instruments.

The description of preferred embodiments of the invention which follows is intended, inter alia, to provide an overview of the bi-plane phased array based invasive imaging apparatus. However, the specific description should not be considered to be a limitation as to the scope of the invention but should be understood that the invention extended to other applications and or devices. In this regard, the term "invasive" ultrasound probe (or instrument or apparatus) is intended to apply to any type of diagnostic instrument that is to be inserted into the human body such as TEE probes, endocavity probes or catheter probes.

In accordance with one aspect of the invention, there is provided an ultrasonic bi-plane imaging probe for invasive medical applications, the probe comprising:

at least one ultrasonic bi-plane transducer mounted at a distal part of the probe and comprising a piezoelectric member and a combination of a first sub-array of transducers disposed on a first surface of the piezoelectric member and a second sub-array of transducers disposed on a second surface of piezoelectric member, the first and second sub-arrays of transducers intersecting each other and being rotated by 90 degrees with respect to each other, the first and second sub-arrays of transducers being superimposed on the first and second surfaces of the piezoelectric member so as to form a unique transducer foot print; and a transducer tip located at the distal part of the probe at which the bi-plane transducer is mounted.

Preferably, the probe further comprises a probe housing and a bendable coupler disposed at a junction between the probe housing and the transducer tip.

Advantageously, the bi-plane transducer is of a curved shape. Preferably, the curved shape is one of convex spherical, concave spherical, convex cylindrical, and concave cylindrical.

Preferably, the bi-plane transducer is mounted linearly with respect to the longitudinal axis of the probe such that one azimuthal axis of the bi-plane transducer is aligned with the longitudinal axis and the acoustic propagation axis of the transducer is perpendicular to the longitudinal axis of the probe.

In another important implementation, the bi-plane transducer is mounted on the probe at an angle between 30 and 60 degrees with respect to the longitudinal axis of the probe.

In a preferred embodiment, the at least one bi-plane transducer comprises a first said bi-plane transducer and a second said bi-plane transducer mounted in the vicinity of the first said bi-plane transducer, and the second bi-plane transducer is rotated with respect to the second bi-plane array transducer through an angle of between 30 and 60 degrees.

In another important implementation, the bi-plane further comprises a conventional phased array transducer mounted on the probe in the vicinity of the bi-plane array transducer.

In another preferred embodiment, the bi-plane imaging probe further comprises a biopsy needle guide for guiding insertion of a biopsy needle. Preferably, the first sub-array of transducers has a scanning plane aligned with the longitudinal axis of the probe and is used for imaging an organ of interest, and the second sub-array of transducers is used for monitoring spatial positioning of the biopsy needle during use thereof.

In accordance with a preferred embodiment of the invention, there is provided an ultrasonic bi-plane combined imaging probe for medical invasive applications, said imaging probe comprising:

a piezoelectric member;

an ultrasonic bi-plane transducer comprising a combination of a first sub-array of transducers on a first surface of said piezoelectric member and a second sub-array of transducers on a second surface of piezoelectric member, the first and the second sub-arrays of transducers intersecting each other and being rotated by 90 degrees with respect to each other, the first and second sub-arrays of transducers being superimposed on the first and second surfaces of the piezoelectric member so as to form a unique transducer footprint; and a linear phased array transducer for transmitting high intensity ultrasonic energy to biologic tissue of interest, the linear phased array transducer being disposed on the probe in the vicinity of the bi-plane transducer;

the bi-plane transducer and the linear phased array transducer being mounted such that the respective acoustic patterns produced thereby intersect at a predetermined distance from the surfaces of the bi-plane and linear phased array transducers.

Preferably, the bi-plane transducer is mounted with the acoustic propagation axis thereof perpendicular to the longitudinal axis of the probe, and the linear phased array transducer forms an angle of less than 180 degrees with the surface of the bi-plane transducer, and the acoustic axis thereof intersects the acoustic axis of the bi-plane transducer at an predetermined distance from the surface of the bi-plane transducer.

In an important implementation, the combined imaging probe further comprises a biopsy needle guide, disposed on the probe in the vicinity of the bi-plane and linear phased array transducers, for guiding insertion of a biopsy needle in an area of intersection of the transducer acoustic patterns of the bi-plane and linear phased array transducers.

In another important implementation, the combined imaging probe and the linear phased array transducer is mounted with the acoustic propagation axis thereof oriented perpendicularly to the longitudinal axis of the probe, with the bi-plane transducer being mounted so as to form an angle of less than 180 degrees with the surface of the linear phased array transducer.

In accordance with yet another aspect of the invention, there is provided an ultrasonic bi-plane imaging ultrasonic probe for use with an imaging system having an imaging system interface, the probe comprising: at least first and second sub-array transducers; and multiplexing circuitry for switching one or the other of the first and second sub-array transducers to the imaging system interface.

In one preferred implementation, the multiplexing circuitry is software controlled by the imaging system.

In a further preferred implementation, the probe includes a probe handle, and functions of the multiplexing circuitry are manually controlled by control means externally disposed on the probe handle.

Further features and advantages of the present invention will be set forth in, or apparent from, the detailed description of preferred embodiments thereof which follows.

DESCRIPTION OF THE PREFERRED EMBODIMENTS

The illustrations in the figures are provided as a help in understanding the invention. It will be understood that illustrations are not to scale and are simplified views of the devices and elements represented therein.

Figure 1:
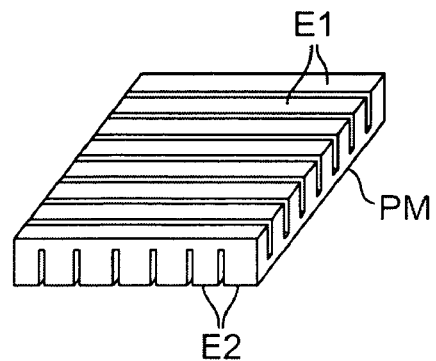
FIG. 1 is a perspective view of a prior art bi-plane phased array transducer.
Figure 2:
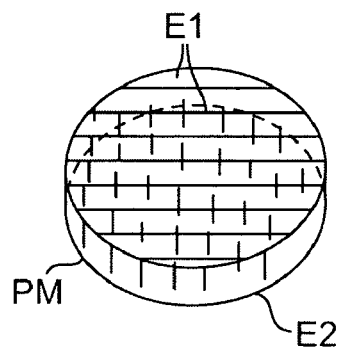
FIG. 2 is a perspective view of a further prior art bi-plane phased array transducer.

FIGS. 1 and 2 depict bi-plane phased array transducers corresponding to those disclosed in the prior art, with the transducers depicted in both FIGS. 1 and 2 being obtained by dicing the electrodes E1 and E2 of a piezoelectric member PM in two perpendicular directions. This dicing can be either exclusively limited to the electrodes E1 and E2 or can partially extend into the piezoelectric material of corresponding piezoelectric member PM. It has been stated in descriptions of this prior art that partial cutting into the piezoelectric material improves acoustic isolation between adjacent elements of the array.

Turning now to the present invention, according to a preferred embodiment of the invention, a main object thereof concerns the provision of ultrasound invasive imaging probes which are equipped with a bi-plane phased array transducer for transmitting and receiving acoustic energy. An important advantage of using a bi-plane phased array transducer is that an instrument or device with multi-view capability can be achieved with a single transducer footprint (no movement of the transducer is necessary) so as to yield to uni-axis crossing scanning planes.

A further object of the invention is to provide a method for providing integration of a bi-plane array transducer, in accordance with a preferred embodiment, into small volume ultrasonic probes that are used in invasive diagnostic instruments. As will appear, this method includes, inter alia, dedicated transducer packaging to minimize space requirements and limit electrical disturbances.

Figure 3:
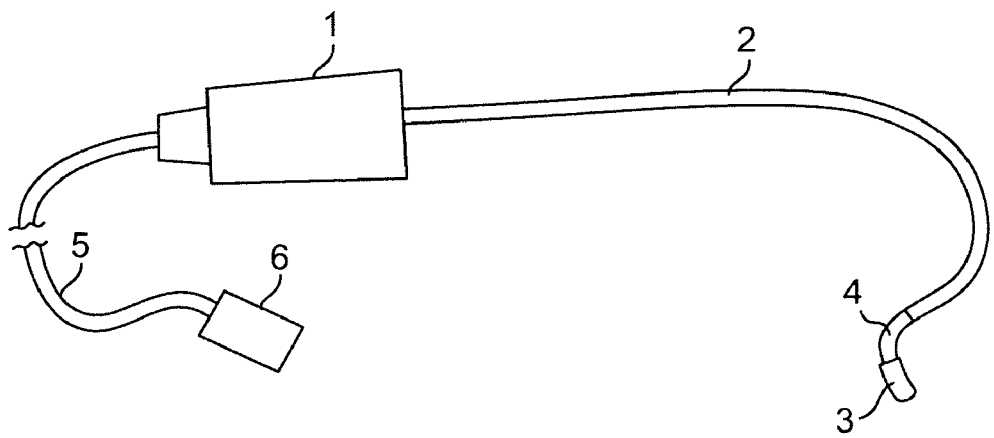
FIG. 3 is a perspective view of an ultrasonic endoscopic probe i.e. a TEE, intravascular, intracardiac type device, in accordance with one embodiment of the invention.
Figure 4:
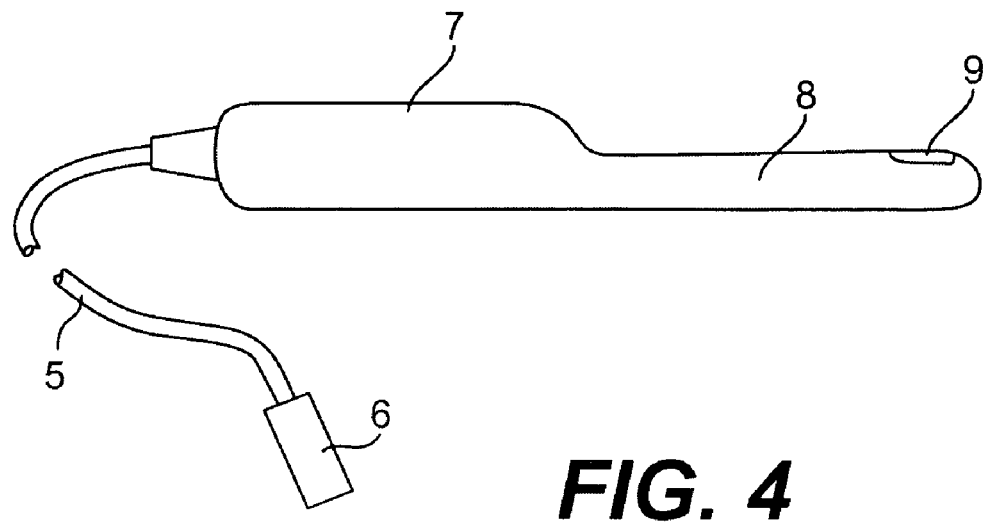
FIG. 4 is a perspective view of an ultrasonic endocavity probe in accordance with a further embodiment of the invention.

Referring first to FIGS. 3 and 4, there are shown invasive probes in the form of an ultrasound endoscopic probe that is illustrated in FIG. 3 and in the form of an endocavity probe that is illustrated in FIG. 4. More specifically, referring to FIG. 3, the endoscopic probe of FIG. 3 is generally composed of a handle 1 which usually acts as receptacle or housing for the steering mechanism for the probe, a long flexible tubular element 2 which is connected to one end of the handle 1 and is terminated by a bendable coupler 4 located at the proximal side of a distal transducer tip 3. The probe also includes a connecting cable 5 and an electrical connector 6. It will be appreciated that invasive instruments such as endoscopes are very widely used for heart diagnosis and the associated transducer typically comprises a high frequency (5–10 MHz) phased array.

As indicated above, FIG. 4 represents an endocavity imaging probe such as is used for endo-vaginal or endo-rectal applications, and similar elements to those of the probe of FIG. 3 have been given the same numbers. In FIG. 4, the probe comprises a handle 7 which is extended by an elongated tube or tubular portion 8 wherein a transducer 9 is mounted. As in FIG. 3, a cable 5 and connector 6 are provided at the opposite side of the handle 7. The transducer 9 may be disposed in the probe in various different ways depending on the application or the organ to be imaged. This aspect will be discussed further below.

Figure 5:
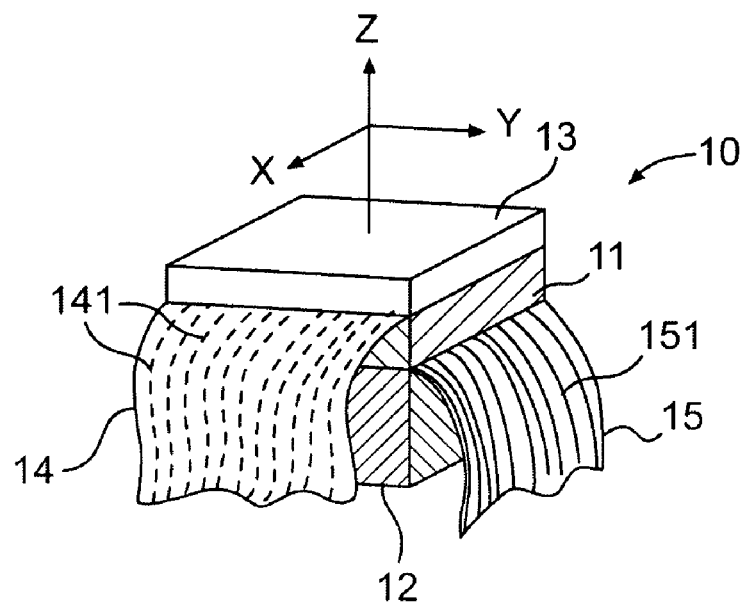
FIG. 5 is a perspective view of a bi-plane transducer in accordance with one embodiment of the invention.

With regard to the transducer itself, a compact, integrated bi-plane array transducer is used in these embodiments. The characteristics of such a transducer are compatible with the utilization thereof in invasive combinations, as was already mentioned. Referring to FIG. 5, there is shown a bi-plane array transducer 10 having a typically square footprint so that the crossing sub-arrays of the transducer 10 are identical. Generally speaking, it is desirable to provide the bi-plane device with the same acoustic and geometric characteristics for both arrays in order provide interchangeability of the transducer array in operation. However, crossing arrays with different dimensions are still feasible if desired.

The transducer 10 of FIG. 5 is comprised of a piezoelectric member 11 which can be implemented as a monolithic structure or a multi-layered structure without any impact on the operation or feasibility of the present invention. The transducer arrays are provided on each of the main surfaces of the piezoelectric member and the elemental transducers are connected, respectively, to a first circuit 14 for the first array and to a second circuit 15 for the second array, with the first and second arrays crossing each other at a 90 degree orientation. A backing member 12 is provided on the rear face of the piezoelectric member 11 and the front face of member 11 is laminated to a plurality of acoustic matching layers 13 in order to enhance the transducer performance.

Although the specific details of the transducer design and construction do not form part of the present invention, it is noted with respect to the materials used that, for instance, the piezoelectric member 11 can be made up of PZT or single crystal or composite, the backing 12 is advantageously produced by mixing and curing a flexible resin with inorganic particles or micro-bubbles incorporated therein, and the matching layers 13 can be provided by laminating different sub-layers of gradient resins. The ultrasonic energy is directed along the Z axis as shown in FIG. 5 and the two crossing arrays are arranged to extend along the X axis and the Y axis, respectively.

Because the array transducers are separately addressed by the system, the flexible circuits 14 and 15 are independent of one another and are connected to the system separately. Each array of the transducer 10 is driven as an phased array and, in an alternate manner, so that when the first array is operational, all of the electrodes of the second array are shunted to the ground of the pulse generator, and vice versa. By addressing the transducer 10 in this way, the bi-plane array transducer 10 is capable of providing all of the features of a conventional single phased array transducer without any compromise as to performance.

Figure 6A:
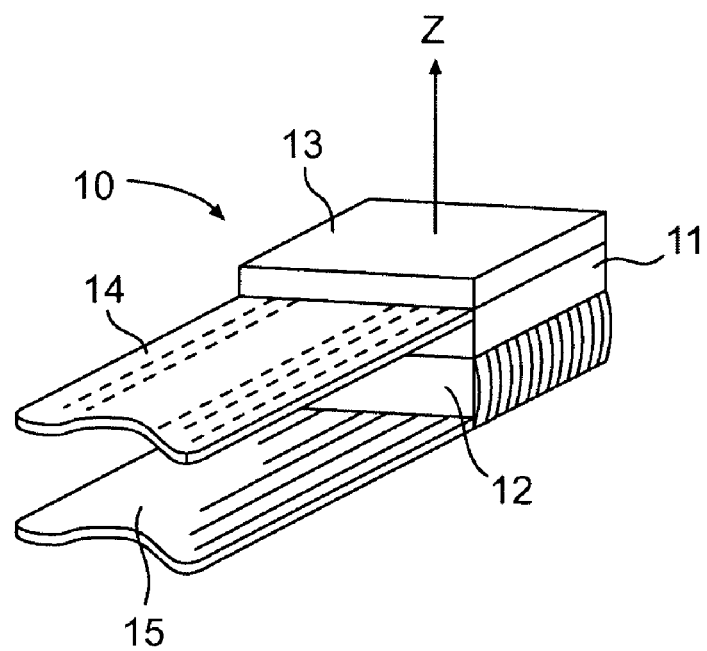
FIGS. 6(a) and 6(b) are different perspective views of a bi-plane interconnection means in accordance with a further embodiment of the invention.
Figure 6B:
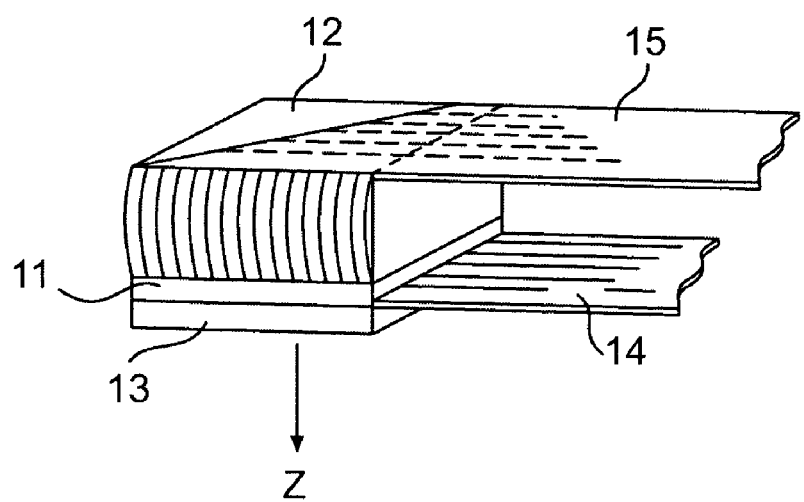

Referring to FIGS. 6(a) and 6(b), as illustrated, the bi-plane array transducer 10 is constructed so that the interconnection circuits 14 and 15 physically extend in parallel with each other in order to facilitate integration of transducer device 10 into a corresponding probe housing. This is achieved by folding flexible circuit 15 as shown in FIG. 6(b) so that circuit 15 extends parallel to circuit 14 rather than orthogonal thereto. The purpose of this construction is to align the two flexible circuits 14 and 15 of the respective arrays in a manner which enables assembly of the circuits 14 and 15 on the same strip and allows a ground plane (not shown) to be provided between the two layers of the circuits. It is, however, to be noted that the folding of the flexible circuit 15 is to be carried out using an insulating thin film (not shown) applied to the folding area, i.e., between the portions of circuit 15 that are folded together and would otherwise be brought into contact. This avoids short-circuiting between the tracks of flexible circuit 15 when the latter is folded.

Figure 7:
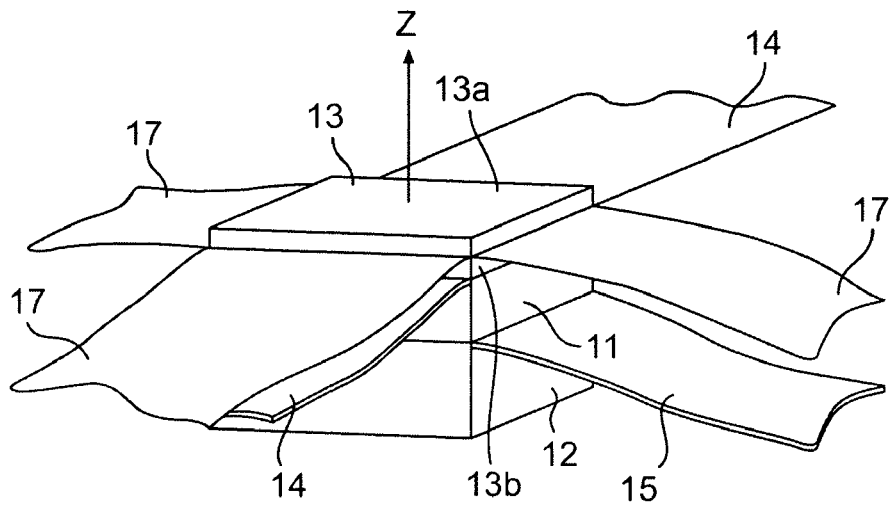
FIG. 7 is a perspective view of a further bi-plane interconnection means.

In another embodiment of the bi-plane array transducer of the invention illustrated in FIG. 7, the transducer is provided with an overall shielding element 17 which is sandwiched between the two layers 13a and 13b of the acoustic matching material 13. Usually, the shielding foil 17 is connected to the general ground plane of the system in order to improve EMI protection level of the probe. However, in some circumstances, the shielding 17 can be instead electrically shunted to the electrical ground of the transducer as well.

Figure 8A:
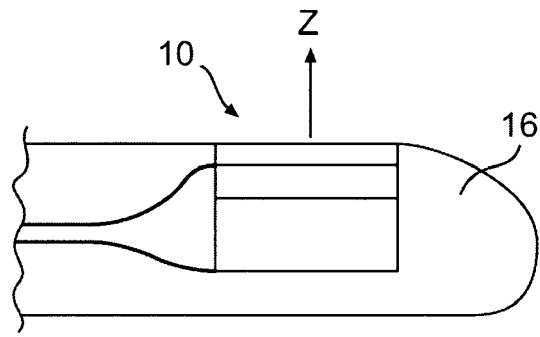
FIGS. 8(a), 8(b), and 8(c) are side elevational views showing different transducer configurations mounted at a transducer tip.
Figure 8B:
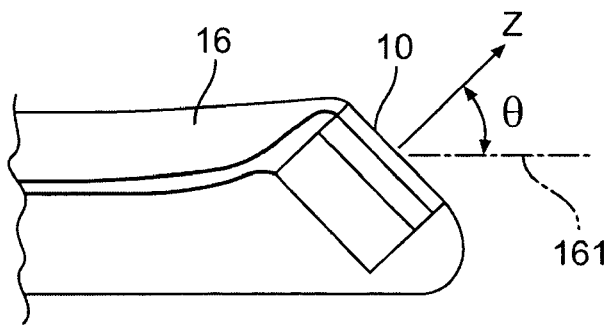
Figure 8C:
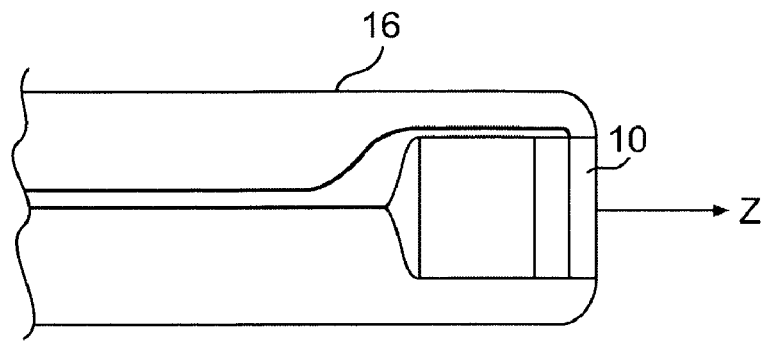

The bi-plane ultrasonic array transducer of the present invention can be employed in a large variety of imaging probes having diverse configurations. Among these are some specific probe configurations commonly used in endocavity applications. FIGS. 8(a), 8(b) and 8(c) illustrate examples of different transducer tip configurations.

In FIG. 8(a), a probe tip 16 is equipped with bi-plane transducer 10 mounted along the longitudinal axis of said probe. Transducer 10 transceives acoustic energy in relation to the surrounding environment in the direction indicated by the arrow z. The transducer 10 can also be oriented around the axis z to form an angle with the longitudinal axis of the probe 16. For simplicity of illustration, this orientation is not shown.

Another embodiment of the transducer tip is illustrated in FIG. 8(b) wherein the bi-plane transducer 10 is obliquely positioned with regard to the longitudinal axis of the probe 16. In this embodiment, the acoustic propagation axis z forms, with the longitudinal axis of the probe 16, an angle which is preferably between 10 and 80 degrees. The imaging probe 16 is therefore of an "end-finger" probe configuration wherein the probe is capable of imaging the field of view located at the front of the probe tip.

Similarly to the probe illustrated in FIG. 8(b), the embodiment of the transducer of FIG. 8(c) includes a transducer 10 but, in this embodiment the transducer 10 is oriented with the acoustic propagation axis z thereof aligned with the longitudinal axis of the probe 16. Similarly to FIG. 8(b), this configuration is also referred to as an "end-finger" device. In general, end-finger transducer configurations such as those of FIGS. 8(b) and 8(c) are suitable for endo-vaginal applications while a configuration with an orthogonal or perpendicular transducer output as shown in FIG. 8(a) is usually used for trans-rectal applications.

Returning again to a more general consideration of transducer constructions for invasive operations, it is noted that bi-plane transducers for ultrasound imaging applications have been disclosed which have a flat footprint configuration. For the most part, this flat construction is imposed by the fact that transducers made from polycrystalline piezoelectric ceramics are fragile and not flexible enough for applications which involve bending. Although the piezoelectric ceramic for the transducers can be supplied in curved shapes, any transducer construction involving the fabrication of transducer elements arranged in two perpendicular directions involves complex problems with respect to the homogeneity between the central elements and the outermost elements located on the periphery of the transducer device. One aspect of the present invention concerns the provision of a bi-plane transducer that enables curving or bending thereof after the array patterns are provided. A transducer in accordance with this aspect of the invention is preferably manufactured from composite materials that advantageously combine piezoelectric performance and flexibility.

Referring to FIGS. 9(a) to 9(d), the composite material forming piezoelectric member 11 is shaped according to the required dimensions of the transducer and both faces thereof have electrodes plated thereon. The array patterns are then provided on each electrode of the composite member 11 to obtain a bi-plane device. Thereafter, interconnect means are provided on the array electrodes and, optionally, front matching layers are bonded to the front surface of the composite. At this stage of fabrication, the transducer can be heat shaped to any type of curvature prior to the addition thereto of a backing member 12 on the rear face of composite.

Figure 9A:
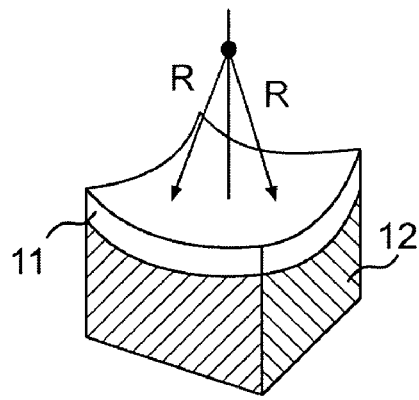
FIG. 9(a) is a perspective view of a concave focused bi-plane transducer in accordance with one embodiment of the invention.

Turning specifically to FIG. 9(a), there is illustrated a transducer of a spherical curvature with the radius of curvature being identical in the two perpendicular directions.

Figure 9B:
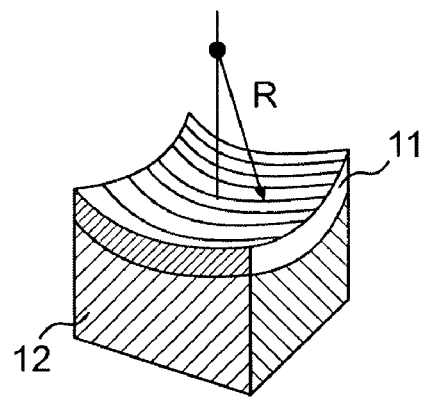
FIG. 9(b) is a perspective view of a concave cylindrically focused bi-plane transducer in accordance with a further embodiment of the invention.

In FIG. 9(b), a cylindrically shaped bi-plane transducer is provided. The concept of enabling bending as described above also results in a bi-plane transducer having a hard focused phased array in one direction and a curved phased array provided on the same transducing surface which extends in an orthogonal or perpendicular direction with respect to the first array. This particular characteristic makes the transducer configuration useful or interesting for some applications where one of the arrays is used for an imaging operation while the other is dedicated to high intensity ultrasound (HIFU) activities.

Figure 9C:
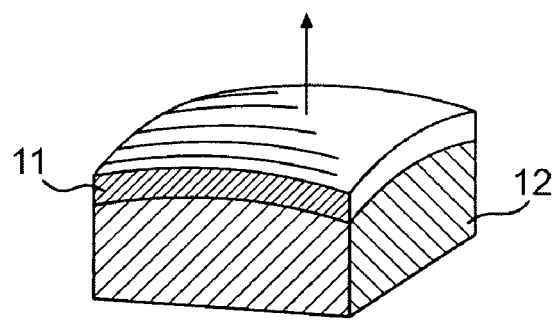
FIG. 9(c) is a perspective view of a convex focused bi-plane transducer in accordance with another embodiment of the invention.
Figure 9D:
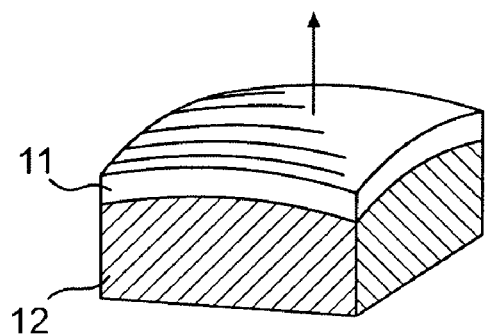
FIG. 9(d) is a perspective view of a convex cylindrically focused bi-plane transducer in accordance with yet another embodiment of the invention.

FIGS. 9(c) and 9(d) illustrate bi-plane transducers having convex curvatures and, in particular, a convex curvature of a spherical shape in FIG. 9(c) and a convex curvature of a cylindrical shape in FIG. 9(d). These configurations of curvature are more suitable for 3D imaging techniques where a wider angle of scanning is desirable.

Figure 10:
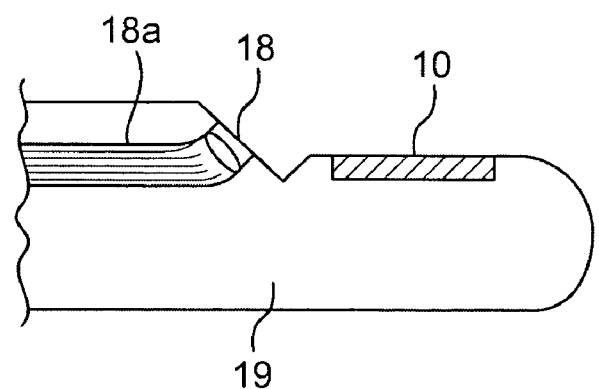
FIG. 10 is a side elevational view of a transducer tip including a flat bi-plane transducer, in accordance with one embodiment of the invention.
Figure 11:
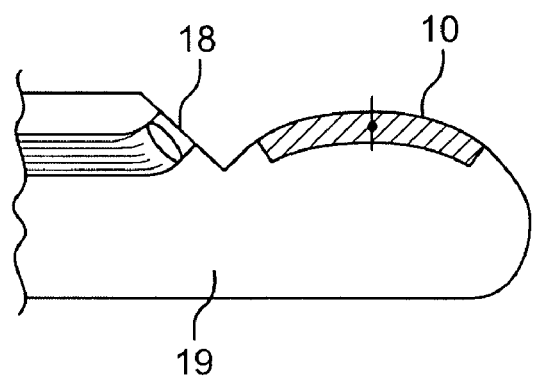
FIG. 11 is a side elevational view of a transducer tip including a convex bi-plane transducer, in accordance with a further embodiment of the invention.
Figure 12:
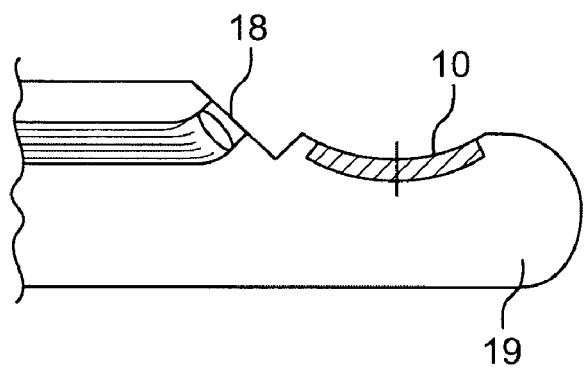
FIG. 12 is a side elevational view of a transducer tip including a concave bi-plane transducer, in accordance with another embodiment of the invention.

Referring to FIGS. 10, 11 and 12, there are shown three examples of a bi-plane transducer 10 incorporated into a respective endoscopic imaging probe 19. In FIG. 10, a flat shaped or planar bi-plane transducer 10 is mounted at the distal tip of the endoscope 19, with the transducer 10 being mounted orthogonal to or perpendicular to the longitudinal axis of the endoscope 19 so as to provide lateral scanning of the organ to be imaged. An optical viewing or visualization accessory, such as an optical fiber 18a or CCD camera module (not shown), can be provided in or at a working channel termination 18 formed in endoscope 19 in the vicinity of the bi-plane array 10. The angle that is formed by the scanning plane of the transducer and the output axis of optical accessory (e.g., the CCD camera module) is chosen so as to enable the user to visually access the region of interest. Further, this part of endoscope 19 can further house a biopsy orifice (not shown) for tissue sampling.

FIG. 11 discloses a configuration of an endoscope 11 with a convex curve shaped bi-plane transducer 10 mounted in the same position as transducer 10 of FIG. 10, while FIG. 12 shows a corresponding concave bi-plane transducer 10. It is noted that transducer 10 as described is related to that of FIGS. 9(a) and 9(d) or FIGS. 9(a) and 9(b).

Figure 13:
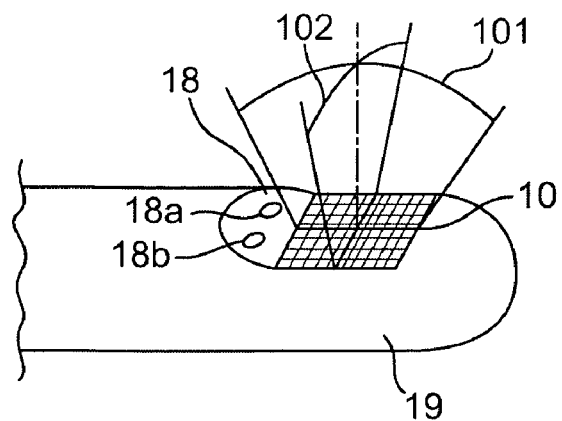
FIG. 13 is a perspective view of a bi-plane transducer mounted in a transducer tip, in accordance with one embodiment of the invention.

Referring to FIG. 13 there is shown an ultrasound imaging endoscope tip 19 having a bi-plane transducer 10 linearly mounted on the transducer tip 19 of the endoscope. It is noted that a bi-plane transducer is referred to as being linearly mounted when at least one of its scanning planes is aligned with the longitudinal axis of the endoscope. The working channel termination 18 in the embodiment of FIG. 13 is provided with orifices 18b and 18c that can received suitable optics or a surgical instrument inserted therein. The transducer 10 is capable of producing a scanning plane, indicated a 101, in alignment with the longitudinal axis of the endoscope tip 19 as well as an intersecting scanning plane, indicated at 102, that is orthogonal to the longitudinal axis.

Figure 14:
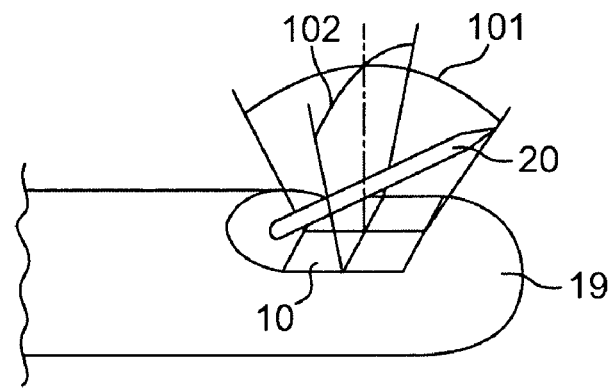
FIG. 14 is a perspective view of a bi-plane transducer and an associated biopsy needle, in accordance with a further embodiment of the invention.

In the further description of the invention which follows, there will be demonstrated the unique advantages of the intersecting scanning planes provided for situations in which a biopsy needle or surgical instrument is used in an endoscopy procedure. In this regard, referring to FIG. 14, there is shown a biopsy needle 20 which is introduced through a working channel 18 of the endoscope tip 19 and is to be placed in the region of interest for tissue sample extraction. As is evident from FIG. 14, the positioning of the biopsy needle 20 is permanently monitored by the scanning plane 102 which extends perpendicular to the transducer tip 19. Further, because the intersection of the two scanning planes 101 and 102 is effectively at the central axis of transducer 10 and the tissue to be sampled can easily be moved to this area of the image, the desired spatial positioning of the biopsy needle 20 can be achieved. This capability of accurately localizing the position of the biopsy needle 20, i.e., accurately controlling the position thereof, is only feasible with a uni-axis intersecting bi-plane transducer such as has been described.

Figure 15:
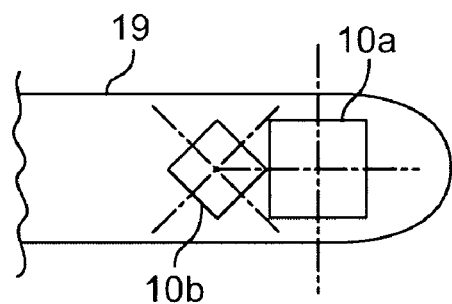
FIG. 15 is a top plan view of a transducer tip configuration comprising two separate bi-plane phased array transducer, in accordance with an embodiment of the invention.

In FIG. 15, there is shown a combination of two bi-plane transducers. As illustrated, on endoscope tip 19 are respectively mounted a first bi-plane transducer 10a which is linear with respect to the endoscope tip 19 and a second bi-plane transducer 10b which is rotated with respect to the first transducer 10a through an angle of between 30 and 60 degrees (and typically 45 degrees as illustrated). The transducers 10a and 10b are shown as being in the near vicinity of one another. The relative physical positioning of the transducers 10a and 10b does not affect the operation thereof. For example, transducer 10a can be mounted forwardly or rearwardly with respect to transducer 10b.

Figure 16A:
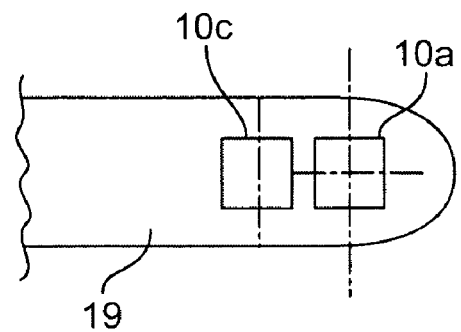
FIG. 16 is a top plan view of a transducer tip comprising a combination of a bi-plane transducer and a conventional phased array transducer, in accordance with another embodiment of the invention.
FIG. 16(b) is a top plan view of another transducer configuration combining a bi-plane transducer and a conventional phased array transducer, in accordance with a further embodiment of the invention.
Figure 16B:
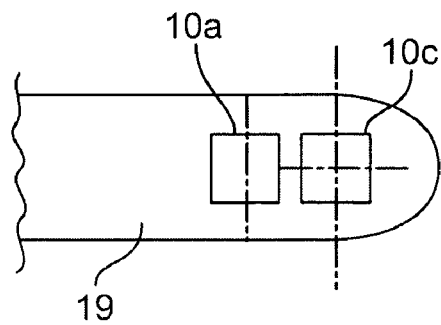

Referring to FIGS. 16(a) and 16(b), there are shown two hybrid combinations used in an invasive imaging probe. As illustrated, in both embodiments, a bi-plane transducer 10a is mounted in combination with a conventional phased array transducer 10c located in the vicinity thereof. It will be appreciated that the embodiment of FIG. 16(b) is a symmetrical or reverse order combination of that of FIG. 16(a). The transducer 10c shown in FIGS. 16(a) and 16(b) is positioned so that the azimuth plane thereof is orthogonal to the longitudinal axis of the endoscope but it will be understood that other orientations of transducer 10c can be used. For instance, transducer 10c can be aligned with the longitudinal axis of endoscope tip 19.

Such a combination of transducers can be of particular interest for combined therapy/diagnostic ultrasonic devices. In this regard, the ultrasonic probe tip 19 includes both the bi-plane imaging transducer 10a which is capable of providing extended viewing of the interested organ and, in the vicinity of the imaging transducer 10c, the high intensity acoustic array transducer 10c which can be used for the treatment of malignant tissues.

Figure 17:
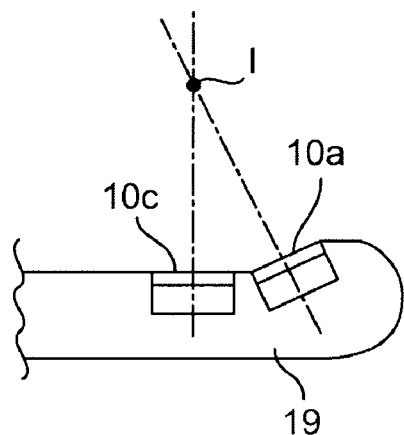
FIG. 17 is a side elevational view of a transducer tip in accordance with yet another embodiment of the invention.

The two transducers 10a and 10c can also be advantageously mounted on oblique surfaces in a manner so that the energy radiated therefrom intersects at a predetermined location. This approach will facilitate the targeting operation of the user as is illustrated in FIG. 17 where the acoustic plane of transducer 10c crosses that of bi-plane transducer 10a at a location denoted point I.

Figure 18:
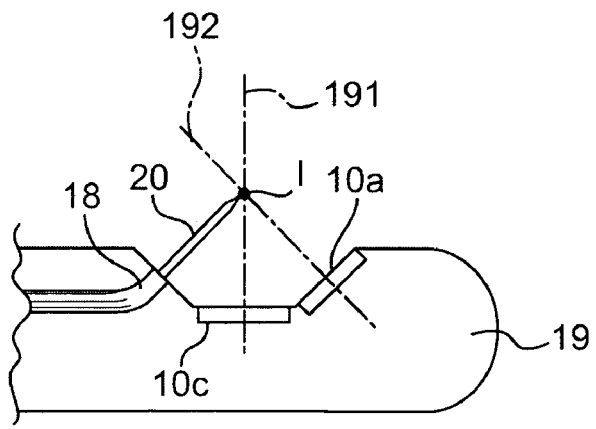
FIG. 18 is a side elevational view of a transducer tip in accordance with still another embodiment of the invention.

A further embodiment of the previously described version of the probe tip 19 is shown in FIG. 18. In this embodiment, the bi-plane imaging transducer 10a and the high intensity array transducer 10c are mounted as already described in connection with FIG. 17, with an intersecting angle provided between the acoustic axes of the two. Additionally, the endoscope tip 19 is further provided with a working channel termination 18 from which extends a biopsy needle 20 or other surgical instrument which can be introduced into the tissue being examined. The insertion path of biopsy needle 20 is predetermined to cross the intersection of the acoustic axes of the transducers 10a and 10c, which is denoted point I. It is also possible for a user to modify the location of the aforementioned intersecting point I.

In FIG. 18, the high intensity transducer 10c has the azimuth plane thereof extending perpendicularly to the longitudinal axis of the endoscope tip 19, and the elements of the array 10c can electronically focus on any point of the vertical axis, denoted 191, containing the point I. In turn, the bi-plane transducer 10a has at least one sub-array wherein the acoustic axis 192 can be made to intersect the axis 191 by electronic steering of the elements of that sub-array. Further, the biopsy needle guide (not shown) for biopsy needle 20 can be equipped with an angle bending control capability preferably located at the outlet termination of the working channel. An ultrasonic probe equipped with all of the above features is capable of focusing on any region within the field of view thereof, is capable of focusing high intensity acoustic energy along the vertical axis 191 of the transducer and is able to extract tissue samples from the region of intersect with accuracy.

The ultrasonic probes and the associated transducers incorporated therein, as described above, provide a number of new imaging capabilities through the use of invasive devices. Using a bi-plane phased array transducer to replace a conventional 1D phased array or a rotating phased array or a 2D array is quite beneficial in that this enables significant simplification of the probe construction. As will be evident, the present invention is particularly suitable for use in invasive imaging apparatus because the small volume of the transducer housing and the avoidance of a rotating mechanism such as is essential in conventional rotating probe devices.

Figure 19:
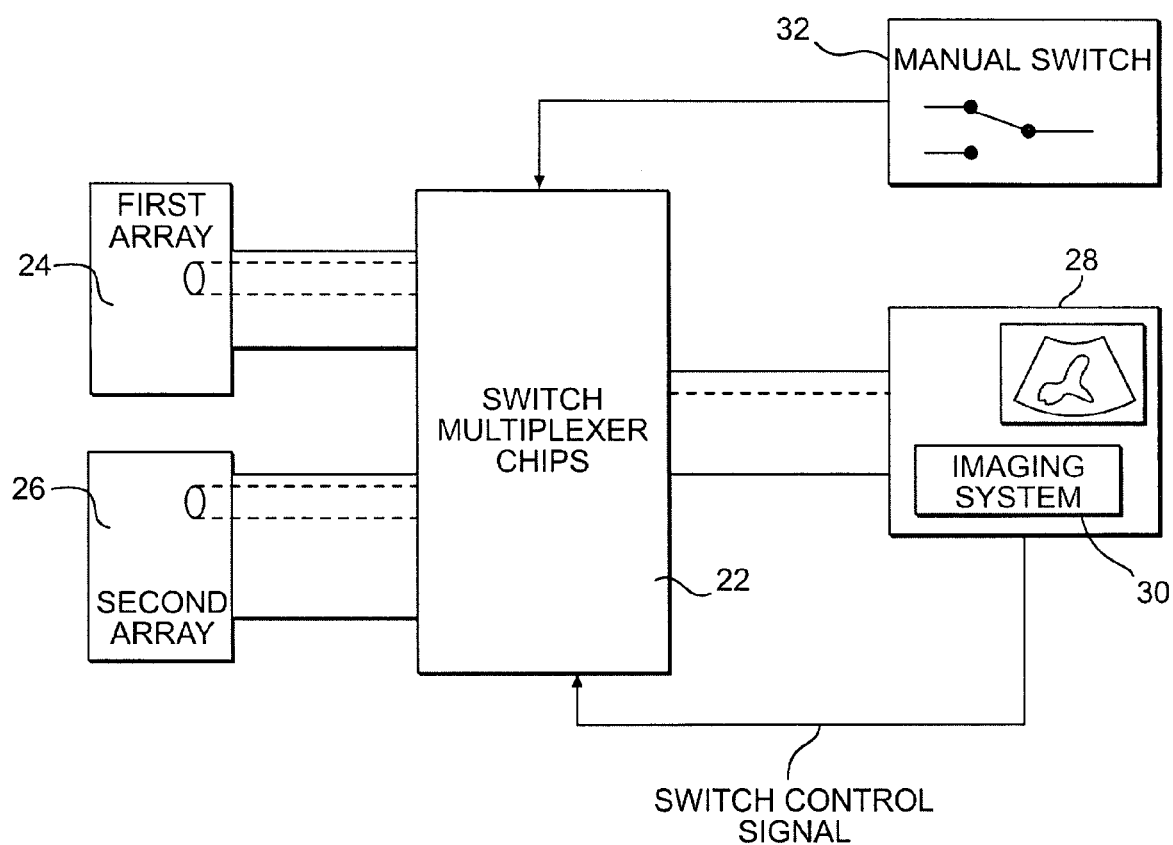
FIG. 19 is a schematic diagram of a further embodiment of the invention.
Figure 20:
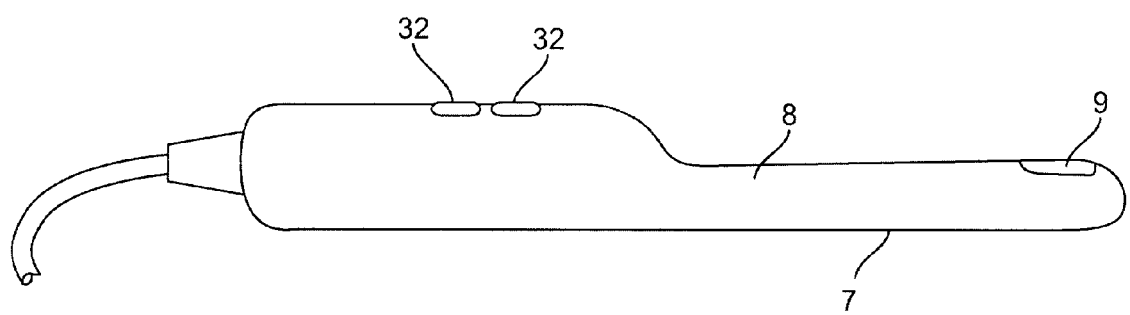
FIG. 20(a) is a general view of an endocavity probe in accordance with one implementation of the embodiment of FIG. 19.
FIG. 20(b) is a general view of an endoscopic probe in accordance with another implementation of the embodiment of FIG. 19.

Referring to FIG. 19, in this embodiment, probes and associated transducers described above can also be provided with multiplexing circuitry disposed between the first and second transducer arrays 24 and 26 and the electronic mainframe 28. As shown, the multiplexing circuitry 22 can be comprised of a plurality of high voltage analog switch/multiplexer chips (ICs) such as those supplied by Supertex (i.e., HV209) of Sunnyvale, Calif. As so equipped a change in the scanning view of the bi-plane ultrasound probe can be readily software controlled by the imaging system 30 of the electronic mainframe 28 or, as shown in FIGS. 20(a) and 20(b) for an endocavity probe and an endoscopic probe, respectively, multiplexing functions can be manually controlled using an external switch controller or other pushbutton controller 32 provided on the probe housing 7.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic bi-plane imaging probe for invasive medical applications, said probe comprising:
   at least one ultrasonic bi-plane transducer mounted at a distal part of the probe and comprising a piezoelectric member and a combination of a first sub-array of transducer electrodes disposed on a first surface of the piezoelectric member and a second sub-array of transducer electrodes disposed on a second surface of piezoelectric member, the first and second sub-arrays of transducer electrodes intersecting each other and being rotated by 90 degrees with respect to each other, the first and second sub-arrays of transducer electrodes being superimposed on the first and second surfaces of the piezoelectric member so as to have a common transducer footprint or a common axis of symmetry;
   first and second flexible interconnection circuits for providing electrical interconnections to said first and second sub-arrays wherein at least one of said interconnection circuits is folded such that the first and second interconnection circuits extend in a common direction; and
   a transducer tip located at the distal part of the probe at which the bi-plane transducer is mounted.

2. An ultrasonic bi-plane imaging probe according to claim 1 wherein the probe further comprises a probe housing and a bendable coupler disposed at a junction between the probe housing and the transducer tip.

3. An ultrasonic bi-plane imaging probe according to claim 1 wherein the bi-plane transducer is of a curved shape to provide geometrical focusing of the bi-plane transducer.

4. An ultrasonic bi-plane imaging probe according to claim 3 wherein said curved shape is one of convex spherical, concave spherical, convex cylindrical, and concave cylindrical.

5. An ultrasonic bi-plane imaging probe according to claim 1 wherein the probe includes a longitudinal axis, the bi-plane transducer has an acoustic propagation axis and the bi-plane transducer is mounted so that the acoustic propagation axis thereof is linearly arranged with respect to the longitudinal axis of the probe.

6. An ultrasonic bi-plane imaging probe according to claim 1 wherein the probe has a longitudinal axis and the bi-plane transducer is mounted on the probe at an angle between 30 and 60 degrees with respect to the longitudinal axis of the probe.

7. An ultrasonic bi-plane imaging probe according to claim 1 wherein said at least one bi-plane transducer comprises a first said bi-plane transducer and a second said bi-plane transducer mounted in the vicinity of the first said bi-plane transducer, and wherein the second bi-plane transducer is rotated with respect to the first bi-plane array transducer through an angle of between 30 and 60 degrees.

8. An ultrasonic bi-plane imaging probe according to claim 1 further comprising a conventional phased array transducer mounted on the probe in the vicinity of the bi-plane array transducer.

9. An ultrasonic bi-plane imaging probe according to claim 1 further comprising a biopsy needle guide for guiding insertion of a biopsy needle.

10. An ultrasonic bi-plane imaging probe according to claim 9 wherein the probe has a longitudinal axis, the first sub-array of transducer electrodes has a scanning plane aligned with the longitudinal axis of the probe and is used for imaging an organ of interest and the second sub-array of transducer electrodes is used for monitoring spatial positioning of the biopsy needle during use thereof.

11. An ultrasonic bi-plane imaging probe according to claim 1 wherein said first and second interconnection circuits extend parallel to one another.

12. An ultrasonic bi-plane combined imaging probe for medical invasive applications, said imaging probe comprising:
   a piezoelectric member;
   an ultrasonic bi-plane transducer comprising a combination of a first sub-array of transducer electrodes on a first surface of said piezoelectric member and a second sub-array of transducer electrodes on a second surface of piezoelectric member, the first and the second sub-arrays of transducer electrodes intersecting each other and being rotated by 90 degrees with respect to each other, the first and second sub-arrays of transducer electrodes being superimposed on the first and second surfaces of the piezoelectric member so as to have a common transducer footprint or a common axis of symmetry; first and second flexible interconnection circuits for providing electrical interconnections to said first and second sub-arrays wherein at least one of said interconnection circuits is folded such that the first and second interconnection circuits extend in a common direction; and
   a linear phased array transducer for transmitting high intensity ultrasonic energy to biologic tissue of interest, the linear phased array transducer being disposed on the probe in the vicinity of the bi-plane transducer;
   the bi-plane and the linear phased array transducers being mounted such that the respective acoustic patterns produced thereby intersect at a predetermined distance from the surfaces of the bi-plane and linear phased array transducers.

13. A combined imaging probe according to claim 12 wherein the probe has a longitudinal axis, the bi-plane transducer has a surface and an acoustic propagation axis, and the bi-plane transducer is mounted with the acoustic propagation axis thereof perpendicular to the longitudinal axis of the probe and the linear phased array transducer forms an angle of less than 180 degrees with the surface of the bi-plane transducer, and the acoustic axis thereof intersects the acoustic axis of the bi-plane transducer at an predetermined distance from the surface of the bi-plane transducer.

14. A combined imaging probe according to claim 12 further comprising a biopsy needle guide disposed on the probe in the vicinity of the bi-plane and linear phased array transducers for guiding insertion of a biopsy needle in an area of intersection of the transducer acoustic patterns.

15. A combined imaging probe according to claim 12 wherein the probe has a longitudinal axis and the linear phased array transducer has a propagation axis, and is mounted with the acoustic propagation axis thereof oriented perpendicularly to the longitudinal axis of the probe, the bi-plane transducer being mounted so as to form an angle of less than 180 degrees with the surface of the linear phased array transducer.

16. An ultrasonic bi-plane imaging probe for invasive medical applications, said probe comprising:
   at least one ultrasonic bi-plane transducer mounted at a distal part of the probe and comprising a piezoelectric member and a combination of a first sub-array of transducer electrodes disposed on a first surface of the piezoelectric member and a second sub-array of transducer electrodes disposed on a second surface of piezoelectric member, the first and second sub-arrays of transducer electrodes intersecting each other and being rotated by 90 degrees with respect to each other, the first and second sub-arrays of transducer electrodes being superimposed on the first and second surfaces of the piezoelectric member so as to have a common transducer footprint or a common axis of symmetry; and
   a transducer tip located at the distal part of the probe at which the bi-plane transducer is mounted,
   the probe including a longitudinal axis, the bi-plane transducer having an acoustic propagation axis and the bi-plane transducer being mounted so that the acoustic propagation axis thereof is co-linear with the longitudinal axis of the probe.

17. An ultrasonic bi-plane imaging probe for invasive medical applications, said probe comprising:
   at least one ultrasonic bi-plane transducer mounted at a distal part of the probe and comprising a piezoelectric member and a combination of a first sub-array of transducer electrodes disposed on a first surface of the piezoelectric member and a second sub-array of transducer electrodes disposed on a second surface of piezoelectric member, the first and second sub-arrays of transducer electrodes intersecting each other and being rotated by 90 degrees with respect to each other, the first and second sub-arrays of transducer electrodes being superimposed on the first and second surfaces of the piezoelectric member so as to have a common transducer footprint or a common axis of symmetry; and
   a transducer tip located at the distal part of the probe at which the bi-plane transducer is mounted,
   said at least one bi-plane transducer comprising a first said bi-plane transducer, and a second said bi-plane transducer mounted in the vicinity of the first said bi-plane transducer, and the second said bi-plane transducer being rotated with respect to the first said bi-plane array transducer through an angle of between 30 and 60 degrees.

* * * * *